United States Patent [19]
Thomas et al.

[11] Patent Number: 5,170,786
[45] Date of Patent: Dec. 15, 1992

[54] REUSABLE PROBE SYSTEM

[75] Inventors: Simon W. H. Thomas, New Haven; Herbert F. D'Alo, Madison, both of Conn.

[73] Assignee: Novametrix Medical Systems, Inc., Wallingford, Conn.

[21] Appl. No.: 807,705

[22] Filed: Dec. 16, 1991

Related U.S. Application Data

[63] Continuation-in-part of Ser. No. 589,349, Sep. 28, 1990, abandoned.

[51] Int. Cl.$^5$ ................................................ A61B 5/00
[52] U.S. Cl. ..................................... 128/633; 128/665
[58] Field of Search ..................... 128/633, 644, 653.1, 128/664-667

[56] References Cited

U.S. PATENT DOCUMENTS

| | | | |
|---|---|---|---|
| 4,726,382 | 2/1988 | Boehmer et al. | 128/667 |
| 4,771,790 | 9/1988 | Yamasawa et al. | 128/667 |
| 4,830,014 | 5/1989 | Goodman et al. | 128/665 |
| 4,865,038 | 9/1989 | Rich et al. | 128/665 |
| 4,928,691 | 5/1990 | Nicolson et al. | 128/664 |
| 5,094,240 | 3/1992 | Muz | 128/666 |

Primary Examiner—Ruth S. Smith
Attorney, Agent, or Firm—Fiddler, Levine & Mandelbaum

[57] ABSTRACT

A probe system for removable attachment to a patient in which the probe containing light emitter and detector elements is separable from a fastener for securing the probe to the skin of a patient to enable the fastener to be discarded and the probe reused. Apertures in the fastener complementary to the probe housings enable secure stabilization of the probe system on the skin and maintain a fixed relationship between the light emitter and detector elements.

10 Claims, 8 Drawing Sheets

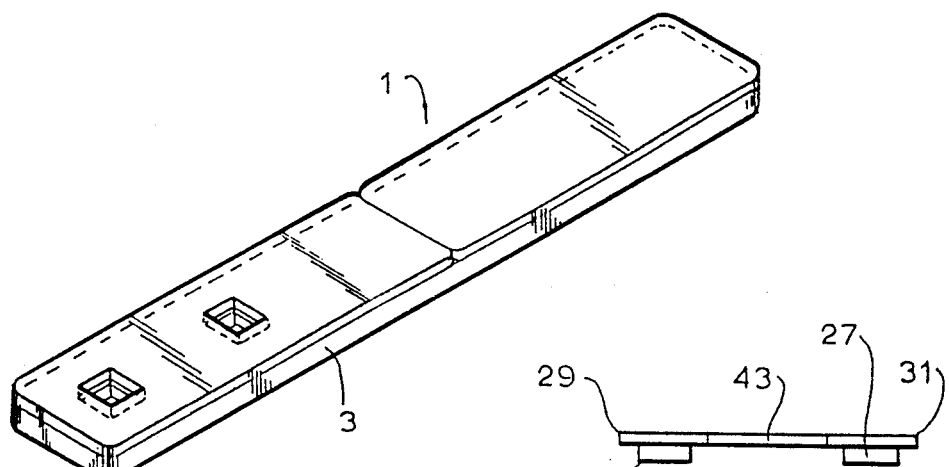
FIG. 1
FIG. 1a
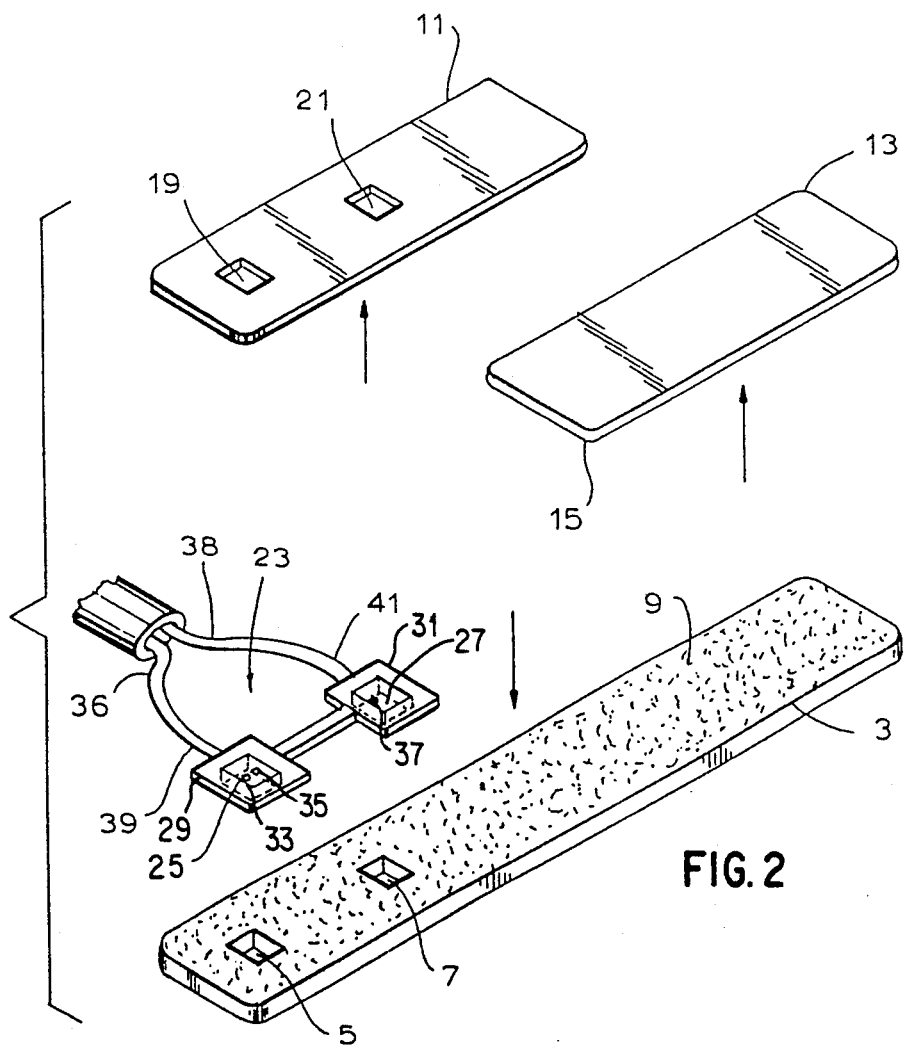
FIG. 2

REUSABLE PROBE SYSTEM

This is a continuation-in-part of application Ser. No. 07/589,349, filed Sep. 28, 1990, now abandoned.

BACKGROUND OF THE INVENTION

This invention is related to sensors applied to the body for monitoring or making measurements of body tissue condition, metabolism or other body functions indicative of health. More specifically, the invention is directed to an appliance which can be readily attached to the body to support a sensor adjacent thereto in a stable disposition for accurate and precise measurements unhampered by artifact due to sensor motion relative to the body.

One application for a probe system of the type described herein is in pulse oximetry, a non-invasive method of measuring the relative oxygen saturation of the blood. Pulse oximeters generally employ light sources, e.g., light emitting diodes (LEDs), to alternately direct light of two different wave lengths, e.g., red and infra-red, to the blood through the skin. The light transmitted or reflected by the blood at the different wave lengths can then be compared to provide a measurement of oxygen saturation.

Typically, a probe system containing the light sources, e.g., LEDs, and a light sensor, e.g., photodetector, is mounted on an appendage of the body, e.g., the finger, toe, ear lobe, nose, hand or foot, although it can be used on virtually any cross section of tissue having pulsatile blood flow which can be penetrated by light emissions from the light source. An example of such a sensor is disclosed in U.S. Pat. No. 4,830,014 to Goodman for Sensor Having Cutaneous Conformance. In the probe system of the aforementioned Goodman patent, the light source and sensor are embedded within a flexible adhesive substrate used for attachment to the appendage. With repeated applications, the adhesive progressively loses its tack. Hence, the adhesive substrate must be frequently disposed of due to loss of adhesive tack as well as for infection control. Because the sensor elements are embedded within the substrate, they too are discarded.

Because the sensor elements account for the most expensive part of the probe system, it is desirable to be able to reuse them and only dispose of the positioning substrate. Until the instant invention, the use of sensor elements separable from a flexible substrate in which the required stability could be achieved in use was unknown.

SUMMARY OF THE INVENTION

The foregoing problems and others associated with prior art probe systems are overcome by the instant invention. The instant invention teaches the construction and method of use of a reusable probe system in which a substrate used to fasten a light source and light sensor in stable disposition on the skin of an appendage can be discarded after use with the light source and light sensor reusable in conjunction with a replacement substrate. More specifically, the instant invention provides for a reusable probe system for attachment to an appendage of a patient including first and second probe elements each disposed in a respective housing having a face through which energy can be transmitted or received and a projection orthogonal to the face; a substantially planar flexible strip to which the first and second probe elements are removably attached, the strip having opposite facing upper and lower outer surfaces through which there extend first and second spaced apertures, the first and second probe element projections being removably disposed in the first and second flexible strip apertures, respectively, so that the probe housing faces are parallel to, and face in the same direction as, the flexible strip upper surface, and fastening means for securing the flexible strip about the appendage with the first and second probe element faces directed toward each other with the appendage therebetween.

It is therefore an object of the invention to provide a probe system adapted for removable attachment to a living body for non-invasively producing signals indicative of a condition of the body.

Another object of the invention is to provide a probe system suitable for repeated use among several patients.

Still another object of the invention is to provide a probe system which is conformable to the surface of the body at which it is positioned thereby resisting motion with respect to the body.

A further object of the invention is to provide a probe system which can be readily disinfected or sterilized between uses.

Still a further object of the invention is to provide a probe system having a very low profile for enhanced flexibility.

An additional object of the invention is to provide a probe system which can be stabilized with respect to an appendage of the body by a separate and disposable adhesive or non-adhesive strip.

Still another additional object of the invention is to provide a probe system which can be stabilized with respect to an appendage of the body by a separate and disposable strip after which the probe system can be reused with a replacement strip.

Still a further additional object of the invention is to provide a probe system which can be optionally secured on the body without the application of adhesive to the body to minimize tissue damage when the probe system is removed from the body.

Other and further objects of the invention will be apparent from the following drawings and description of a preferred embodiment of the invention in which like reference numerals are used to indicate like parts in the various views.

DESCRIPTION OF THE DRAWINGS

FIG. 1 is a perspective view of a part of a first preferred embodiment of the invention.

FIG. 1a is an elevation view of another part of the preferred embodiment of the invention.

FIG. 2 is an exploded perspective view of the first preferred embodiment of the invention.

DESCRIPTION OF THE PREFERRED EMBODIMENTS

Figure 3:
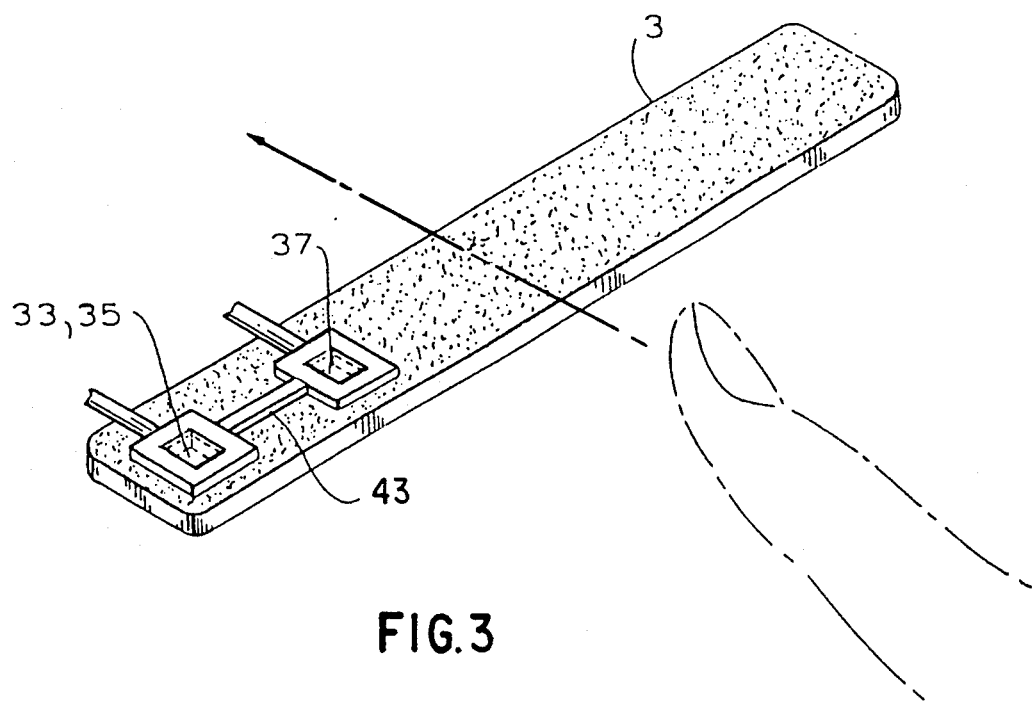
FIG. 3 is a perspective view of a portion of the first preferred embodiment of the invention prepared for use in its intended environment.

Referring now to FIGS. 1, 1(a), and 2 of the drawings, there is shown a disposable fastener system 1, in accordance with the invention. The disposable fastener system 1, as shown, is used as part of an oximeter probe system, including an infrared light source and sensor, for the measurement of percent oxygen saturation of the blood. However, it is to be appreciated that the structure disclosed herein may have application in other measurements or monitoring of body condition, function or metabolism where it is desired to mount a probe system on the body of a patient.

The disposable fastener system includes a substantially rectangular low profile flexible plastic foam material substrate 3 having two axially aligned spaced square apertures 5 and 7. The upper surface of the foam substrate 3 as viewed in FIGS. 1 and 2 is coated with a thin adhesive layer 9 suitable for removably adhering the foam substrate 3 to the surface of the skin.

As packaged for shipment and storage prior to use, the disposable fastener system has two rectangular planar flexible plastic, or plastic coated paper, cover strips 11 and 18 releasably fastened to the adhesive upper surface of the foam substrate 3. The materials from which the foam substrate 3, adhesive layer region 9 and cover strips 11 and 13 are fabricated are selected so that the adhesive layer region 9 has a greater affinity for the foam substrate 3 than for the cover strips 11 and 13.

Strip 11 is optionally provided with apertures 19 and 21 which are congruent to and in respective alignment with, apertures 5 and 7 when cover strips 11 and 13 are adhered to foam substrate 3.

A sensor probe 23 includes respective housings 25 and 27 which are each in the shape of a geometric rectangular solid, one face of which is framed by an integral rectangular flange 29, 31. The housings 25 and 27 which are preferably formed from a soft pliant rubber-like material serve as projections, extending outwardly from the planes of the flanges 29 and 31, which can be received in the apertures 5 and 7 of the foam strip 3 as will be explained below.

A red light emitting diode 33 and an infrared light emitting diode 35 are adjacently mounted in housing 25 in disposition to alternately radiate red and infrared energy through the housing face framed by the flange 29. The framed face should be transparent to the energies radiated by the LEDs 33 and 35 and preferably is formed from a transparent soft pliant rubber-like material.

As is known in oximetry, the transmission of light in the red range of the spectrum, i.e., at a wave length of approximately 660 nanometers through blood is substantially affected by the amount of oxygenated hemoglobin present in the blood. The transmission of light in the infra-red range of the spectrum, i.e., at a wave length of approximately 940 nanometers through blood is substantially unaffected by the amount of oxygenated hemoglobin present in the blood. Oximeters use this principal to alternately illuminate the blood through the skin tissue with light of the foregoing respective wave lengths. Hence, in accordance with the present invention, the LED 33 emits light in the red range at 660 nm and the LED 35 emits light in the infra-red range at approximately 940 nm.

Mounted in the housing 27 is a photodetector 37 for transmitting signals to an oximeter or other monitor (not shown) in response to received red and infrared light. The photodetector 37 is sensitive to red light and infrared light and is mounted in housing 27 in disposition to receive and sense alternately radiated red and infrared energy through the face framed by the flange 31. The framed face should be transparent to the energies radiated by the LEDs 33 and 35 and, like the transmitting face of housing 25, is preferably formed from a transparent soft pliant rubber-like material.

The LEDs 33 and 35 are connected to a monitor (not shown) via cable 36 which cable extends from a semi-cylindrical stand-off 39 into which the cable is hermetically sealed and which standoff is integral with the housing 25. Similarly, the photodetector 37 is connected to the monitor via cable 38 which extends from a hollow hermetically sealed semi-cylindrical standoff 41 integral with the housing 27. The housings 25 and 27 are optionally connected by an integral bridge member 43 formed from the same material as, or one having characteristic similar to, the soft pliant rubber-like material from which the housings 25 and 27 are formed. The bridge member 43 may be omitted entirely, removably affixed to the housings 25 and 27 so that sensor spacing may be controlled as the probe system 23 is attached to the body and removed before final attachment of the substrate 3, or permanently attached to the housings 25 and 27.

The minor sections of the projections formed by housings 25 and 27 are substantially congruent to the apertures 5 and 7 respectively. This enables the housings 25 and 27 to be respectively inserted through the apertures 5 and 7 until the undersides of the flanges 29 and 31 engage and adhere to the adhesive layer region 9 surrounding apertures 5 and 7 after cover strips 11 and 13 are removed from foam substrate 3 as shown in FIG. 3.

Figure 4:
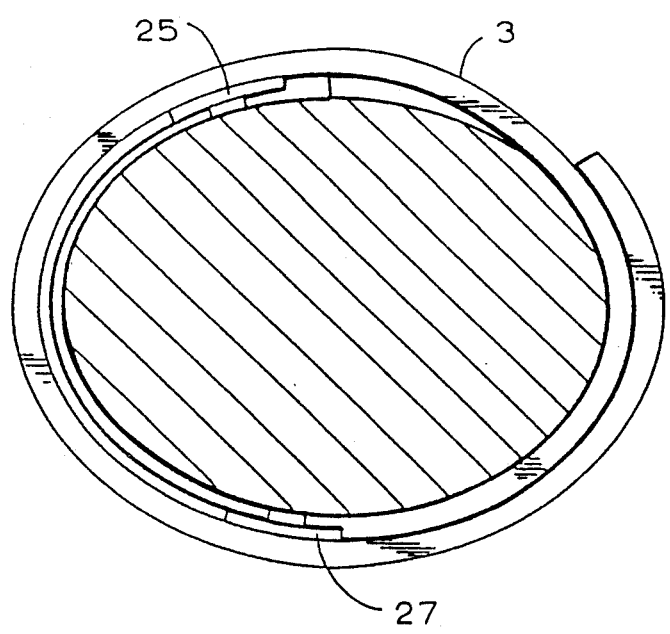
FIG. 4 is a sectional view of the first preferred embodiment of the invention in use in its intended environment.

In use, the cover strips 11 and 13 are separated from the foam substrate 3 after which the housings 25 and 27, which are projections extending from the flanges 29 and 31, are inserted through the apertures 5 and 7 as shown in FIG. 3. Thereafter, the probe system is affixed to a patient by adhering the foam substrate 3 to a body part so that the flanges 29 and 31 and the energy-transparent housing faces they surround engage the skin. With the probe system in this position, the LEDs 33 and 35 in housing 25 and the photodetector 37 in housing 27 are separated by the tissue of the body part and oppose and are directed toward one another to enable light emitted by the LEDs 33 and 35 to pass through the body tissue and impinge upon the photodetector 37. The free end of the foam substrate 3, most distant from the probe 23 is then wrapped around the body part and itself as shown in FIG. 4 so that the adhesive layer region 9 adheres to the skin of the body part and to the opposite surface of the foam substrate 3.

After use of the probe 23 on the patient is completed, the probe 23 may be separated from the foam substrate 3, only the latter then being discarded. The probe 23 may later be sterilized and affixed to another patient with a new foam substrate 3 as described above.

Figure 5:
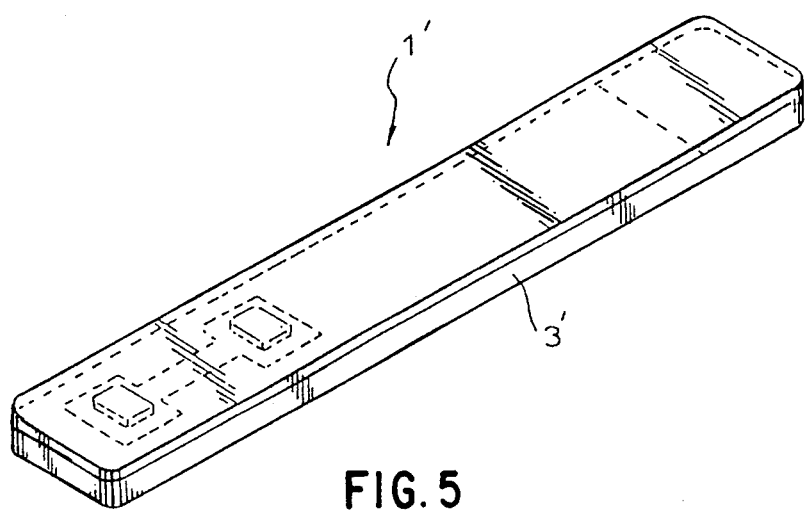
FIG. 5 is a perspective view of a part of a second preferred embodiment of the invention.
Figure 6:
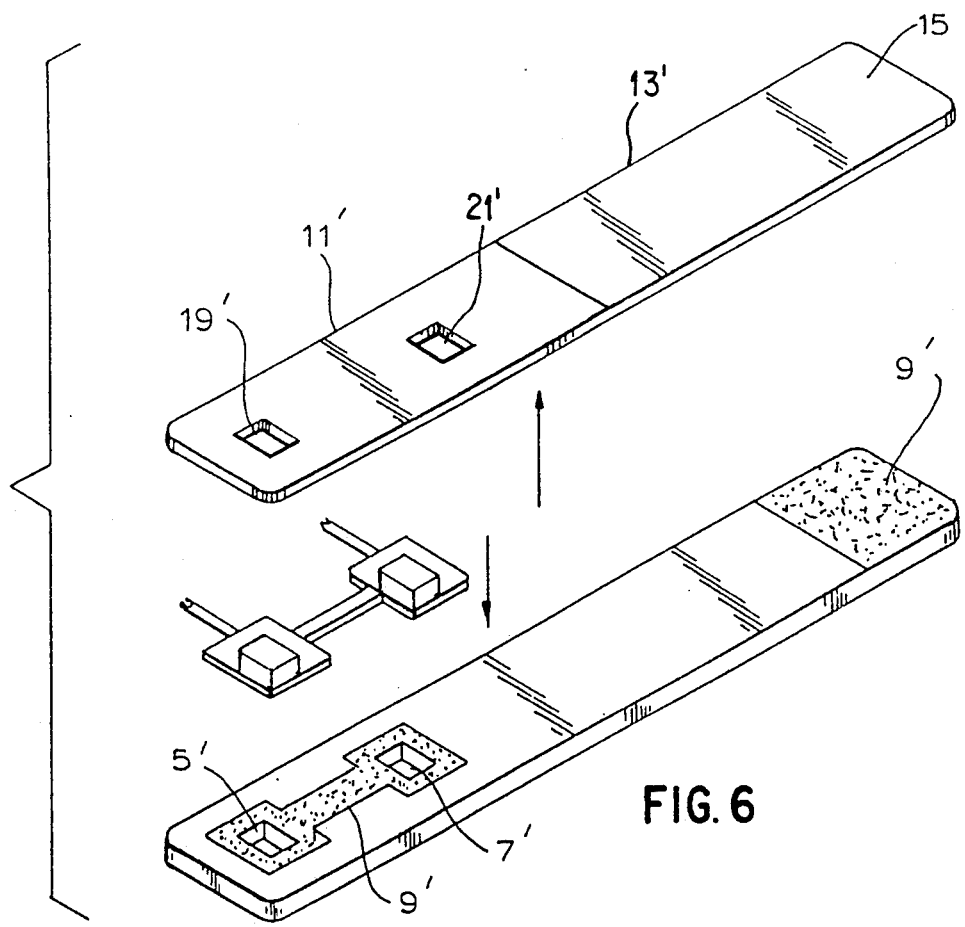
FIG. 6 is an exploded perspective view of the second preferred embodiment of the invention.

Referring now to FIGS. 5 and 6 of the drawings, there is shown a first alternate disposable fastener system 1', in accordance with the invention. The first alternate disposable fastener system includes a substantially rectangular low profile flexible plastic foam material substrate 3' having two axially aligned spaced square apertures 5' and 7'. The upper surface of the first alternate foam substrate 3' as viewed in FIGS. 5 and 6 is coated with a thin adhesive layer 9' suitable for removably adhering the first alternate foam substrate 3' to itself at a small rectangular region adjacent to its free end most distant from the apertures 5' and 7'. A coating of adhesive layer 9' suitable for removably adhering the flanges 29 and 31 and, if present, the optional bridge member 43, of the probe system 23 to the first alternate foam substrate 3' is also provided around and between the apertures 5' and 7' as best seen in FIG. 6. If the optional bridge member 43 is not to be included on the probe system 23, there is a coating of adhesive provided around the apertures 5' and 7' to receive the flanges 29 and 31, but no adhesive coating between the apertures 5' and 7' in the region not covered by the flanges 29 and 31 so that no adhesive contacts the skin when the probe system 23 is applied to the body.

As packaged for shipment and storage prior to use, the disposable fastener system has two rectangular planar flexible plastic (or plastic coated paper) cover strips 11' and 13' releasably fastened to the adhesive regions 9' of the foam substrate 3'.

Strip 11' is optionally provided with apertures 19' and 21' which are congruent with and in respective alignment with apertures 5' and 7' when cover strips 11' and 13' are adhered to foam substrate 3'.

Figure 7:
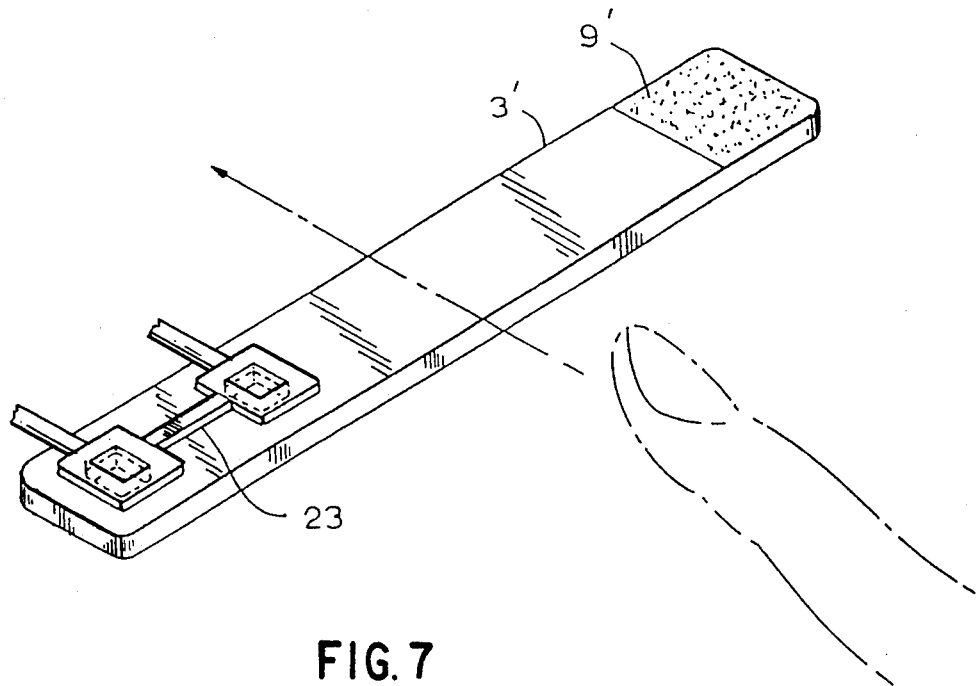
FIG. 7 is a perspective view of a portion of the second preferred embodiment of the invention prepared for use in its intended environment.
Figure 8:
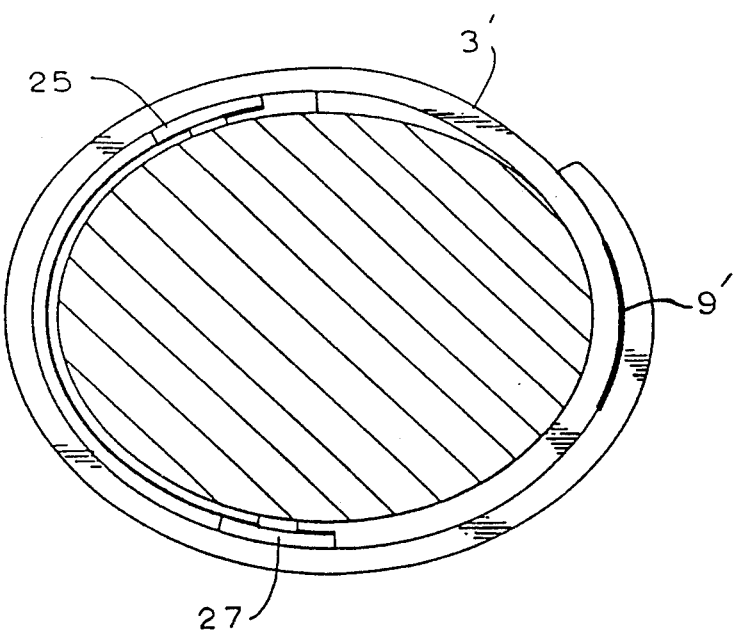
FIG. 8 is a sectional view of the second preferred embodiment of the invention in use in its intended environment.

In use, the cover strips 11' and 13' are separated from the foam substrate 3' after which the housings 25 and 27, which serve as projections extending from the flanges 29 and 31, are inserted through the apertures 5' and 7' as shown in FIG. 7. Thereafter, the probe system disposable fastener system 1' is affixed to a body part of a patient by engaging the foam substrate with the body part so that the LEDs 33 and 35 in housing 25 and the photodetector 37 in the housing 27 are separated by the tissue of the body part, and oppose and are directed toward one another to enable light emitted by the LEDs 33 and 35 to pass through the body tissue and impinge upon the photodetector 37. The free end of the foam substrate 3', most distant from the probe 23, is then wrapped around the body part and itself as shown in FIG. 8 so that the adhesive layer region 9' at its end adheres to the opposite surface of the foam substrate 3'. This embodiment of the invention avoids any contact of adhesive with the skin thereby minimizing tissue damage upon its removal.

After use of the probe system disposable fastener system 1', the foam substrate 3' can be discarded and the probe 23 reused as described above with respect to the first embodiment of the invention.

Figure 9:
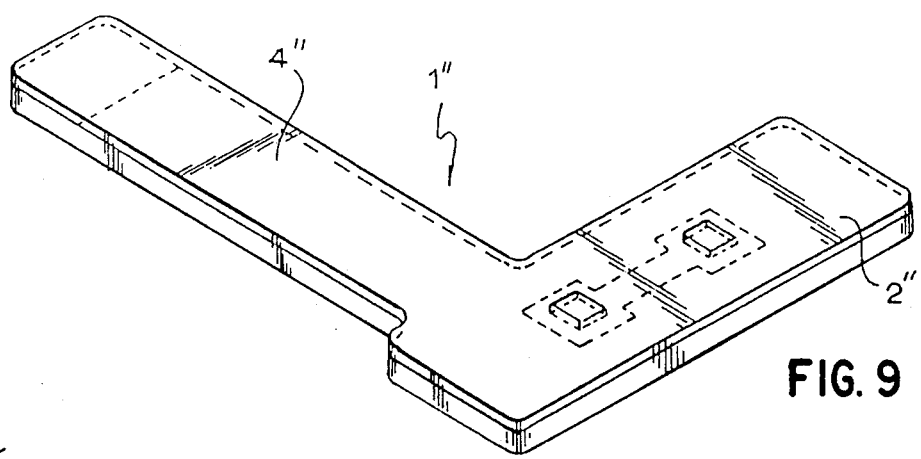
FIG. 9 is a perspective view of a part of a third preferred embodiment of the invention.
Figure 10:
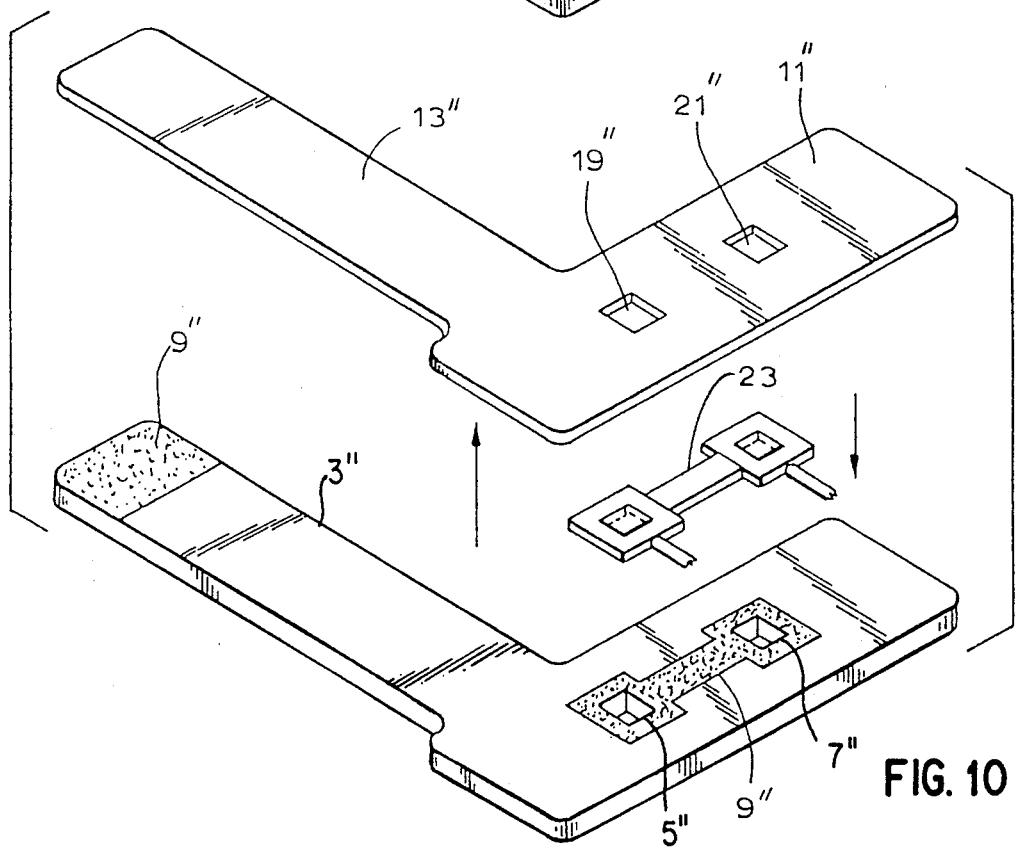
FIG. 10 is an exploded perspective view of the third preferred embodiment of the invention.

Referring now to FIGS. 9 and 10 of the drawings, there is shown a second alternate disposable fastener system 1", in accordance with the invention. The disposable fastener system 1" includes a substantially rectangular L-shaped low profile flexible plastic foam material substrate 3" having a first leg 2" with two axially aligned spaced square apertures 5" and 7". The upper surface of an orthogonal leg 4" of substrate 3", as viewed in FIGS. 9 and 10, is coated with a thin adhesive layer 9" suitable for removably adhering the foam substrate 3" to itself at a small rectangular region adjacent to the free end of the substrate 3" leg most distant from the leg 2" of the 3". A coating of adhesive layer 9" suitable for removably adhering the flanges 29 and 31 and the bridge member 43 of the probe system 23 to the foam substrate" is also provided around and between the apertures 5" and 7" as best seen in FIG. 10.

As packaged for shipment and storage prior to use, the disposable fastener system 1" has two rectangular planar flexible plastic (or plastic coated paper) cover strips 11" and 13" releasably fastened to the adhesive regions 9" of legs 2" and 4" of substrate 3", respectively.

Strip 11" is optionally provided with apertures 19" and 21" which are congruent with and in respective alignment with apertures 5" and 7" when cover strips 11" and 13" are adhered to foam substrate 3".

Figure 11:
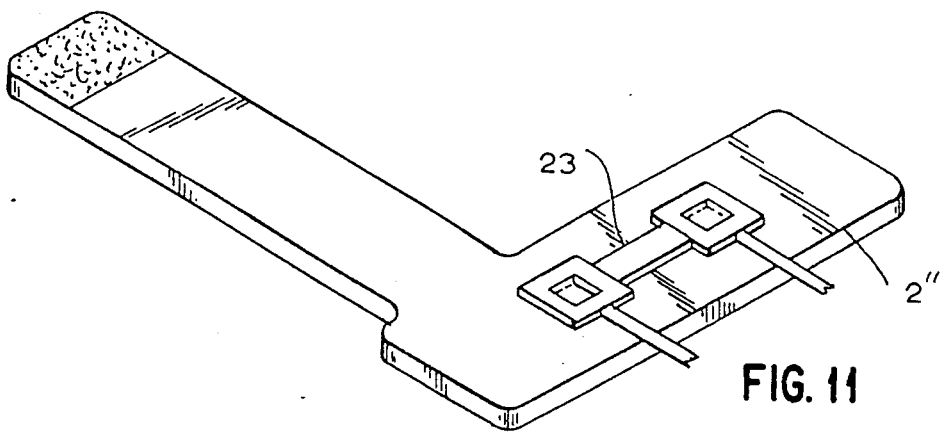
FIG. 11 is a perspective view of a portion of the third preferred embodiment of the invention prepared for use in its intended environment.
Figure 12:
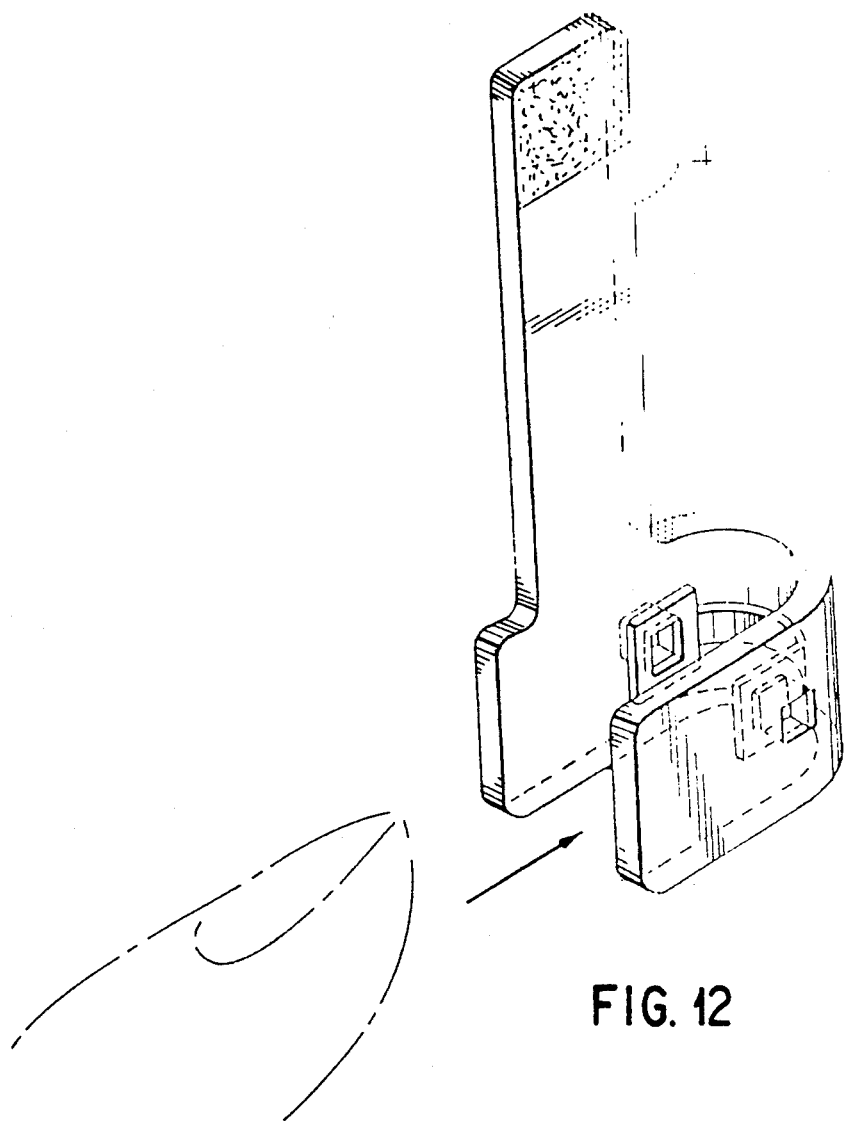
FIG. 12 is a perspective view of the third preferred embodiment of the invention further prepared for use in its intended environment.
Figure 13:
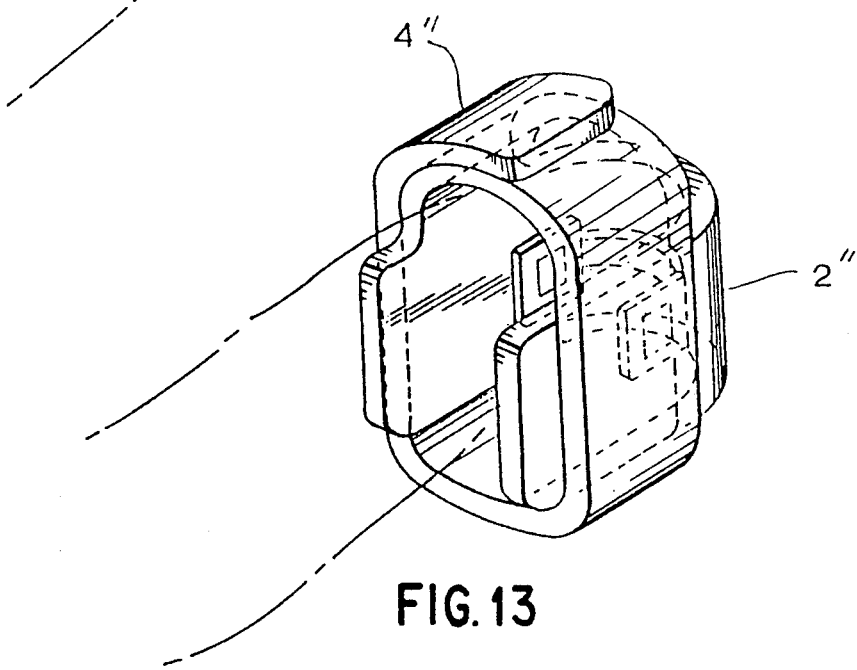
FIG. 13 is a perspective view of the third preferred embodiment of the invention in its intended environment.

In use, the cover strips 11" and 13" are separated from the foam substrate 3" after which the housings 25 and 27, which are projections extending from the flanges 29 and 31, are inserted through the apertures 5" and 7" as shown in FIG. 11. Thereafter, the probe system is affixed to a body part of a patient by engaging the foam substrate 3" with the body part so that the LEDs 33 and 35 in housing 25 and the photodetector 37 in housing 27 are separated by the tissue of the body part, and oppose and are directed toward one another to enable light emitted by the LEDs 33 and 35 to pass through the body part tissue and impinge upon the photodetector 37 with the leg 2" of the substrate 3" wrapped around the body part and the leg 4" extended outwardly as shown in FIG. 12. Thereafter, the free end of the leg 4" of substrate 3" most distant from the probe 23, is then wrapped over the body part and adhered to the foam substrate as shown in FIG. 13 so that the adhesive layer region 9'", at the end of the leg 4" of substrate 3" adheres to the substrate 3".

After use of the probe system, the foam substrate 3" can be discarded and the probe 23 reused as described above with respect to the first embodiment of the invention.

Figure 14:
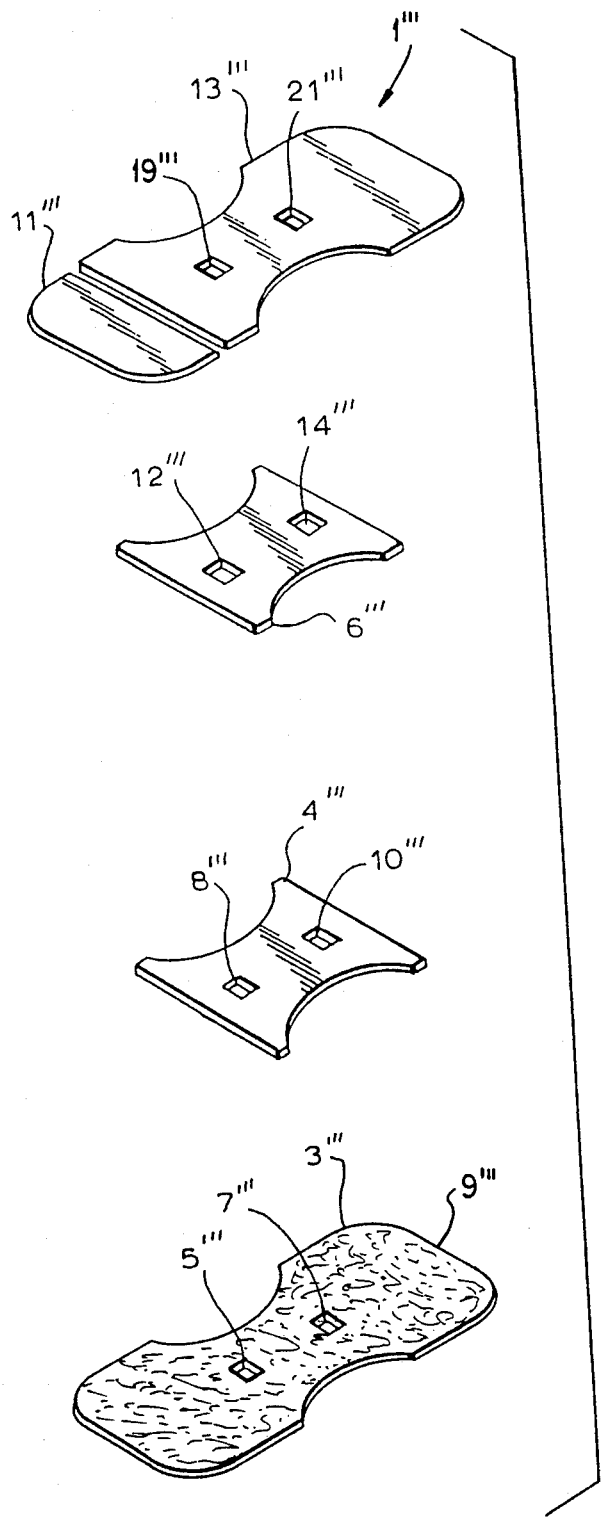
FIG. 14 is an exploded view of a fourth preferred embodiment of the invention.

Referring now to FIG. 14 of the drawings, there is shown a third alternate disposable fastener system 1'" in accordance with the invention. The disposable fastener system 1'" includes a substantially butterfly shaped low profile flexible plastic foam material substrate 3'", the upper surface of which is coated with a thin adhesive layer 9'" suitable for removably adhering the foam substrate 3''' to human skin. The substrate 3''' has two rectangular apertures 5''' and 7'''.

A thin flexible planar light shield, preferably formed from a sheet of mylar coated with gold on one surface and silver on the other, and opaque to light except at two rectangular apertures 8''' and 10''', respectively congruent with apertures 5''' and 7''', is adhesively affixed to the upper surface of substrate 3''' with its apertures in alignment with apertures 5''' and 7''' of substrate 3'''.

Overlying the light shield 4''' and congruent with it is a layer of tape 6''' with apertures 12''' and 14''', preferably made of polyethylene and coated on both sides with layers of adhesive. The adhesive layer on the underside of the tape 6''' adheres the tape to the upper surface of the light shield 4'''. The adhesive layer on the top surface of the tape 6''' forms an essentially continuous adhesive surface with the adhesive on the uncovered end portions of the foam substrate 3'''. This adhesive surface releasably receives planar flexible plastic (or plastic coated paper) cover strips 11''' and 13'''.

Strip 13''' is optionally provided with apertures 19''' and 21''' which are congruent with and in respective alignment with apertures 5''' and 7''', 8''' and 10''' and 12''' and 14''' when cover strips 11''' and 13''' are adhered to tape 6'''.

Figure 15:
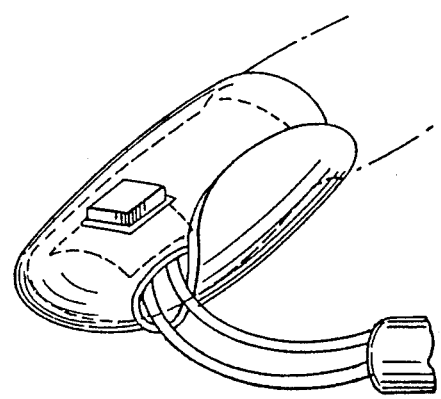
FIG. 15 is a perspective view of the fourth preferred embodiment of the invention in its intended environment.

In use, the cover strips 11''' and 13''' are separated from the foam substrate 3''' and tape 6''' after which the housings 25 and 27, which are projections extending from the flanges 29 and 31, are inserted through the aligned apertures 5''' and 7''', 8''' and 10''', and 12''' and 14'''. Thereafter, the probe system is affixed to a body part, normally a fingertip, of a patient by engaging the tape 6''' with the body part and bending it over the end of the finger so that the LEDs 33 and 35 in housing 25 and the photodetector 37 in housing 27 are separated by the tissue of the finger, and oppose and are directed toward one another to enable light emitted by the LEDs 33 and 35 to pass through the finger tissue and impinge upon the photodetector 37. Thereafter, the sides of the substrate 3''' and tape 6''' are squeezed together to adhere as shown in FIG. 15.

After use of the probe system, the fastener system 1''' can be discarded and the probe 23 reused as described above with respect to the first embodiment of the invention.

Figure 16:
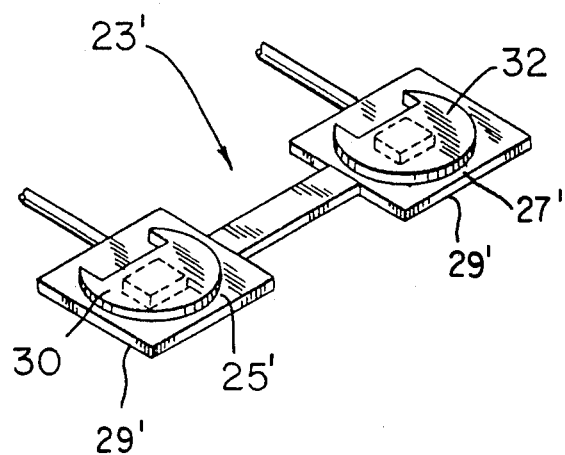
FIG. 16 is a perspective view of a part of a fifth preferred embodiment of the invention.
Figure 17:
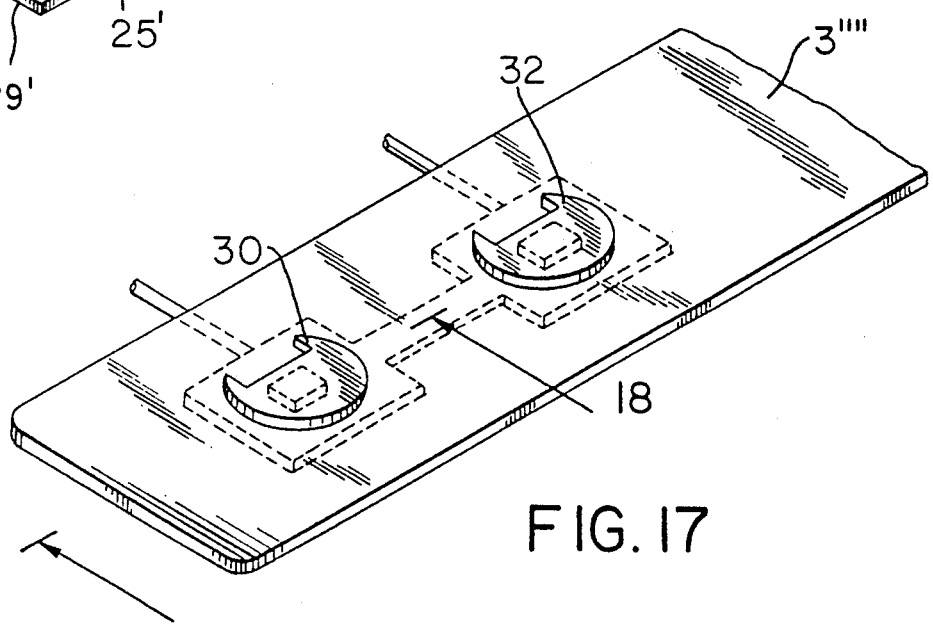
FIG. 17 is a perspective view of a part of the assembled parts of the fifth preferred embodiment of the invention.
Figure 18:
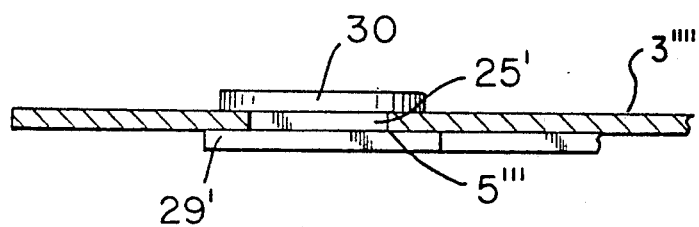
FIG. 18 is a sectional elevation view of the fifth preferred embodiment of the invention taken through line 18—18 of FIG. 17.

Referring now to FIG. 16 of the drawings, there is shown a sensor probe 23' which includes respective housings 25' and 27' which are each in the shape of a geometric rectangular solid, one face of each being framed by an integral rectangular flange 29' and the opposite faces of which are covered by integral, partially rounded ears 30 and 32. The ears 30 and 32 extend beyond the perimeters of the respective housings 25' and 27'. In FIG. 17, a disposable fastener 3'''' includes a substantially rectangular low profile flexible plastic foam material substrate having two axially aligned spaced square apertures 5'''' congruent with the cross section of the rectangular central portions of the housings 25' and 27'. Because of the elastomeric nature of the fastener 3'''' the substrate can be stretched as the ears 30 and 32 are inserted through the apertures 5'''', and thereafter, relaxed, leaving the housings 25' and 27' secured within the apertures 5''''. As can be seen in FIG. 18, the ears 30 and 32 on one side of the fastener 3'''' and a flange 29' on the other side of each aperture of the fastener 3'''' prevent the sensor probe 23' from inadvertently separating from the fastener 3''''. In fact, no adhesive is necessary on the fastener 3'''' to hold the sensor probe 23' in place. The strip 3''' can be fastened to the body as shown in any of the previously described embodiments.

It is to be understood and appreciated that alterations, modifications and variations of and to the preferred embodiment described herein may be made without departing from the spirit and scope of the invention which is defined in the following claims.

What is claimed is:

1. A reusable probe system for attachment to a part of a patient's body comprising:

first and second probe elements each disposed in a respective housing having an energy-transparent face with a surrounding flange and a projection orthogonal to said face;

a substantially planar flexible strip to which said first and second probe element housings are removably attached, said strip having opposite facing upper and lower outer surfaces in which there are first and second spaced apertures, said first and second probe element housing projections being removably disposed in said first and second flexible strip apertures, respectively, so that said probe housing faces are parallel to, and face in the same direction as, and said flanges engage, said flexible strip upper surface, and fastening means adapted for securing said flexible strip about said body part with said first and second probe element housing faces directed toward each other and said body part therebetween.

2. A reusable probe system for attachment to a body part of a patient according to claim 1 wherein said flexible strip is substantially L-shaped with first and second portions having respective substantially orthogonal longitudinal axes, said spaced apertures being disposed in said first strip portion and said second strip portion circumscribing said first strip portion when said reusable probe system is attached to said body part.

3. A reusable probe system for attachment to a body part of a patient according to claim 1 wherein said flexible strip is substantially butterfly shaped for attachment to a finger.

4. A reusable probe system for attachment to a body part of a patient according to claim 1, 2 or 3 wherein said fastening means comprises a layer of adhesive coated onto said flexible strip upper surface for adhering said upper surface to said body part and/or to said lower surface when said strip is wrapped around said body part.

5. A reusable probe system for attachment to a body part of a patient according to claim 1, 2 or 3 wherein said fastening means comprises a layer of adhesive coated onto said flexible strip upper surface adjacent an end thereof for adhering said lower surface to said upper surface when said strip is wrapped around said body part.

6. A reusable probe system for attachment to a body part of a patient according to claim 1 further comprising a bridge member having upper and lower surfaces, a first end connected to said first probe housing and a second end connected to said second probe housing, said bridge upper surface facing in the same direction as said strip upper surface and said bridge lower surface facing in the same direction as said strip lower surface, the distance between said first and second probe elements with said bridge member fully extended being substantially equal to the distance between said first and second apertures.

7. A reusable probe system for attachment to a body part of a patient according to claim 6 wherein said bridge member is removably connected to said first and second probe housings.

8. A reusable probe system for attachment to a body part of a patient according to claim 6 wherein at least one of the upper surface of said strip and the lower surface of said bridge member is coated with an adhesive for affixing said bridge member to said strip.

9. A reusable probe system for attachment to a body part of a patient according to claim 1 wherein at least one of said strip and said flange is coated with an adhesive for affixing said flange to said strip.

10. A reusable probe system for attachment to a part of a patient's body comprising:
   first and second probe elements each disposed in a respective housing having an energy-transparent face with a surrounding flange, a projection orthogonal to said face, and an ear-shaped member mounted on said projection in spaced relationship to said flange;
   a substantially planar flexible strip to which said first and second probe element housings are removably attached, said strip having opposite facing upper and lower outer surfaces in which there are first and second spaced apertures, said first and second probe element housing projections being removably disposed in said first and second flexible strip apertures, respectively, so that said probe housing faces are parallel to, and face in the same direction as said flexible strip upper surface, said flanges and ear-shaped members extending beyond the perimeters of said apertures for preventing said probe element housings from inadvertently separating from said flexible strip, and
   fastening means adapted for securing said flexible strip about said body part with said first and second probe element housing faces directed toward each other and said body part therebetween.

* * * * *